United States Patent
Arocha (10) Patent No.: US 9,896,394 B2
(45) Date of Patent: Feb. 20, 2018

(54) METHOD FOR IMPROVING PROPANE DEHYDROGENATION PROCESS

(71) Applicant: National Industrialization Company, Jubail (SA)

(72) Inventor: Pablo Rafael Arocha, Al Jubail (SA)

(73) Assignee: National Industrialization Company, Jubail Petrochemicals Complex, Jubail Industrial, Jubail (SA)

( * ) Notice: Subject to any disclaimer, the term of this patent is extended or adjusted under 35 U.S.C. 154(b) by 0 days.

(21) Appl. No.: 15/134,948

(22) Filed: Apr. 21, 2016

(65) Prior Publication Data

US 2017/0305814 A1 Oct. 26, 2017

(51) Int. Cl.

| | |
|---|---|
| C07C 5/00 | (2006.01) |
| C07C 7/167 | (2006.01) |
| C07C 5/09 | (2006.01) |
| C07C 5/05 | (2006.01) |
| C07C 7/00 | (2006.01) |
| C07C 5/333 | (2006.01) |
| C07C 7/04 | (2006.01) |

(52) U.S. Cl.
CPC .............. *C07C 5/09* (2013.01); *C07C 5/05* (2013.01); *C07C 5/3332* (2013.01); *C07C 7/00* (2013.01); *C07C 7/04* (2013.01); *C07C 2521/04* (2013.01); *C07C 2523/26* (2013.01); *C07C 2523/44* (2013.01); *C07C 2523/75* (2013.01)

(58) Field of Classification Search
None
See application file for complete search history.

(56) References Cited

U.S. PATENT DOCUMENTS

| 4,753,667 A * | 6/1988 | O'Connell | C07C 7/04 |
| | | | 62/620 |
| 6,218,589 B1 * | 4/2001 | Cottrell | C07C 5/3337 |
| | | | 585/258 |
| 6,414,205 B1 * | 7/2002 | Stanley | C07C 7/005 |
| | | | 203/19 |

(Continued)

FOREIGN PATENT DOCUMENTS

| CN | 101993327 B | 8/2013 | |
| WO | WO 2010070030 A2 * | 6/2010 | B01J 23/44 |

OTHER PUBLICATIONS

Stefan Brejc, et al., "Selective MAPD Hydrogenation in an Existing CATOFIN® PDH Unit", The Catofin Conference, Sep. 2005, 20 pages.

*Primary Examiner* — Philip Louie
(74) *Attorney, Agent, or Firm* — Howard C. Lee (57) ABSTRACT

A propane dehydrogenation and propylene purification process in which a stream comprising propylene, propane, and methyl acetylene and propadiene (MAPD) is mixed with a hydrogen stream then reacted in at least three distinct reaction zones in a hydrogenation reactor system where MAPD is hydrogenated by a high-selectivity hydrogenation catalyst in a first reaction zone, and a second and a third reaction zones each have a low-selectivity hydrogenation catalyst to remove unreacted hydrogen. The outlet stream leaving the hydrogenation reactor system is MAPD-free and can be fed to a splitter column, which now mainly serves to separate propylene from propane. Various embodiments of reaction zone arrangements in a single or multiple reactors are also provided.

14 Claims, 9 Drawing Sheets

(56) References Cited

U.S. PATENT DOCUMENTS

| | | |
|---|---|---|
| 7,319,176 B2 | 1/2008 | Ryu et al. |
| 7,842,847 B2 | 11/2010 | Panditrao et al. |
| 8,013,201 B2 | 9/2011 | Panditrao |
| 2004/0176652 A1* | 9/2004 | Molinier ................ C10G 45/32 585/265 |
| 2011/0054227 A1* | 3/2011 | Cheung ................ B01J 20/0207 585/16 |
| 2016/0332932 A1* | 11/2016 | Montalbano ............ C07C 7/163 |

* cited by examiner

METHOD FOR IMPROVING PROPANE DEHYDROGENATION PROCESS

BACKGROUND OF THE INVENTION

Technical Field

The present invention relates to a method for improving propane dehydrogenation processes. Specifically, the present invention relates to processes for converting dehydrogenation by-products such as methyl acetylene and propadiene (MAPD) from a $C_3$ dehydrogenation process to reduce catalyst deactivation and/or fouling/coking.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Propylene is the world's second largest petrochemical commodity and is used in the production of polypropylene, acrylonitrile, acrylic acid, acrolein, propylene oxide and glycols, plasticizer oxo alcohols, cumene, isopropyl alcohol and acetone. The growth in propylene production is primarily driven by the industry demand for polypropylene, which is used in such everyday products as packaging materials and outdoor clothing.

Propylene is primarily produced from the dehydrogenation of propane. A conventional propane dehydrogenation process involves the following steps: dehydrogenation of propane to propylene in a reactor, compression of the reactor effluent, and recovery and purification of the propylene product.

Figure 1:
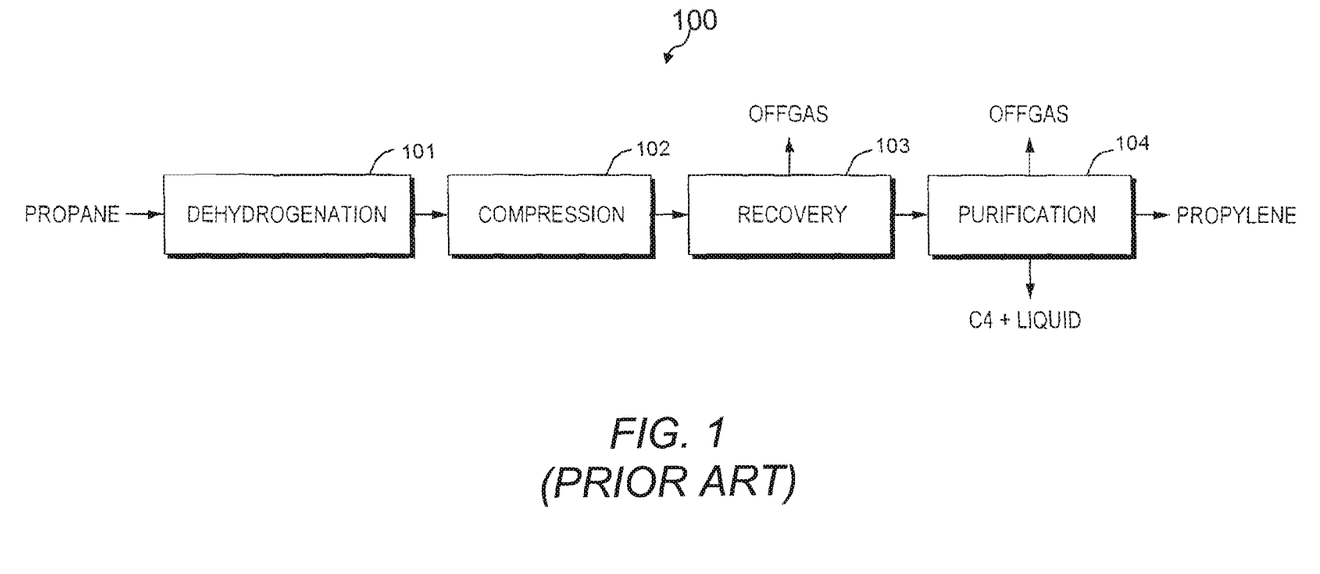
FIG. 1 illustrates a conventional prior art scheme for producing propylene from dehydrogenation of propane.
Figure 2:
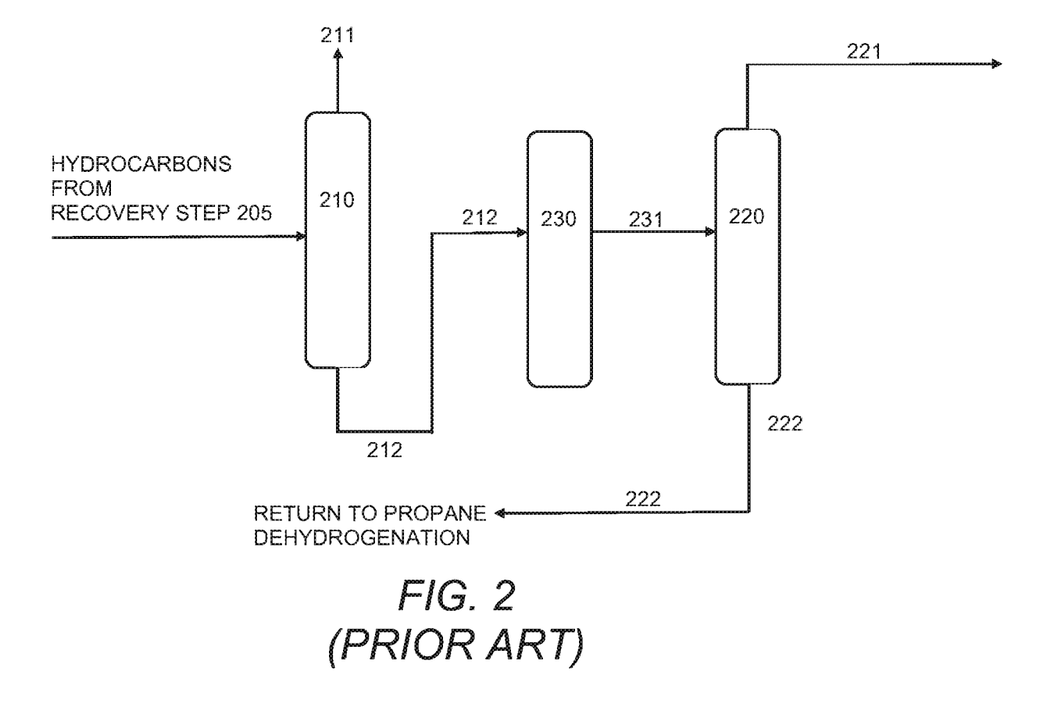
FIG. 2 illustrates a scheme for the purification step of the prior art propane dehydrogenation process of FIG. 1 and the subsequent step to purge MAPD with a propylene product slip stream.

FIG. 1 shows the steps in a conventional dehydrogenation process 100. In the dehydrogenation step 101, the conversion of propane to propylene is typically carried out over a catalyst. In the compression step 102, the effluent from the dehydrogenation unit is compressed in a compressor to a sufficiently high pressure, typically 150 psig or greater, to recover unreacted propane and propylene from lighter components in a recovery section. In the recovery step 103, the compressed reactor effluent is successively chilled with refrigeration to maximize the recovery of propane and propylene for further purification. The offgas from this process is mainly hydrogen, methane, ethane and ethylene. The hydrocarbons from the recovery step 103 are then subjected to distillation in the purification step 104 that is shown in FIG. 2. In a first distillation column, which is a deethanizer 210, ethane and lighter gases are recovered as overhead offgas 211, and propane, propylene and by-products are recovered in the deethanizer bottom stream 212 that becomes the feed stream to a desulfurization unit 230, and the desulfurized effluent 231 from the desulfurization unit becomes the feed stream to a second distillation column that is generally referred to as a product splitter column 220. In the product splitter column 220, propylene product is recovered as an overhead stream 221 and a bottom stream containing unconverted propane and other by-products including methyl acetylene and propadiene (MAPD) 222 is recycled back to the dehydrogenation step. The bottom stream 222 contain also a slip stream of propylene, which is produced through gradual increase of propylene as the propane recycles through the reactors of the Catofin dehydrogenation process. The slip stream of propylene is adapted to remove the MAPD and unconverted propane. The propylene and MAPD present in the recycle stream facilitate coke formation, when the recycle stream is dehydrogenated in the Catofin dehydrogenation reactors. Formation of coke significantly affects the life of the dehydrogenation catalysts present in the $C_3$ Catofin dehydrogenation reactors, and results in a significant reduction of propylene production. The propylene slip stream cannot be recovered; therefore, it is cracked and/or dehydrogenated at the reactors of the $C_3$ Catofin process.

During purification, the product splitter is typically reboiled by using an external heat source (e.g. heat pump) whereby the overhead vapor is compressed and used as the reboiling medium. Hence, the propane-propylene splitter column is used to separate the propylene produced from the unconverted propane, and other heavy compounds. The propane-propylene splitter column is also utilized to regulate the concentration of the MAPD by the slip stream of propylene.

Figure 3A:
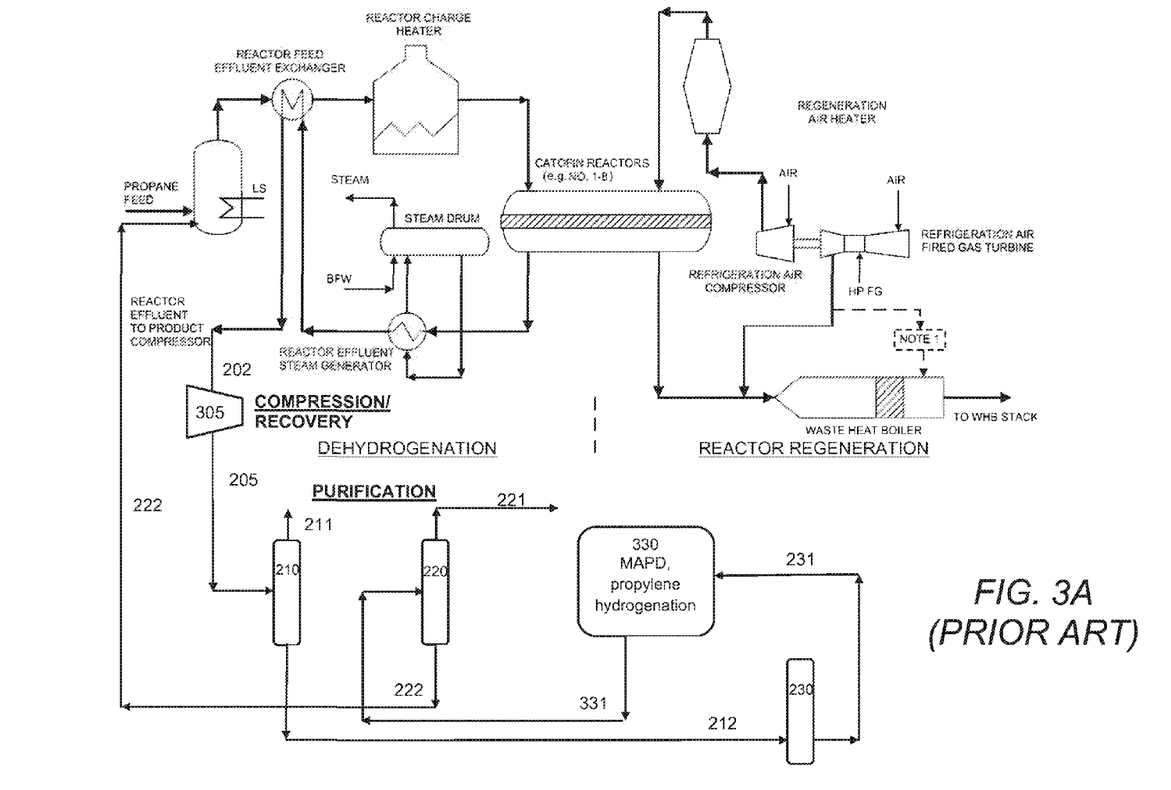
FIG. 3A illustrates a conventional prior art scheme for producing propylene from dehydrogenation of propane at a $C_3$ Catofin process, which combines the dehydrogenation, regeneration, compression/recovery and purification processes or steps.

One common process for production of propylene by dehydrogenation of propane is known as the Catofin process, as shown in FIG. 3A. In the Catofin process, propane is converted to propylene by feeding propane to a dehydrogenation reactor containing affixed bed chromium-alumina catalyst. There are typically multiple dehydrogenation reactors operating in parallel to allow catalyst regeneration to occur in some reactors (i.e. reactors on purge) while others are in operation (i.e. reactors on stream). The dehydrogenation reactors are typically maintained at about 600-650° C.

The effluent from the dehydrogenation reactors is cooled and compressed using a steam driven product compressor. The compressed product is sent to a recovery section where inert gases, hydrogen and light hydrocarbons are removed from the compressed reactor effluent. The propylene-rich gas from the recovery unit is then sent to the product purification section where propylene is separated from propane as described above.

During the production step of the Catofin process, in addition to propylene, different by-products or impurities are formed. The formation of the by-products increases with the aging of the catalyst, which is generated by the combination of its operating conditions and time. Other factors that impact the aging of the catalyst are related to the quality of the feed, and the high or low severity used to operate the plant. Regarding the increment of the generation of by-products, it needs to be highlighted that the event is considered normal at the Catofin technology, and is indicative of the reduction of the selectivity or capability of the catalyst to convert propane into propylene. The impurities or by-products produced during the process, especially the unsaturated ones like acetylene, ethylene, methyl acetylene (MA) and propadiene (PD), affect the product specification of the propylene and they must be removed.

Most of the impurities, except MAPD are eliminated during the finishing of the product, at the distillation section of the unit, which includes the deethanizer that removes $C_2$ components such as ethane, ethylene and acetylene as an overhead stream, the desulfurization unit that removes sulfur, and the $C_3$ propane-propylene splitter column. In this case, the Catofin technology does not establish its conversion to other chemical compounds or materials, but only establishes the control of its concentration in the final product, utilizing a slip stream of propylene from the bottom of the propane-propylene splitter distillation column or splitter column. In addition to the unconverted propane, the splitter column separates the propylene produced from the by-products. However, in circumstances when concentration of MAPD is not monitored, MAPD concentration may rise beyond certain levels (e.g. about 60 mol %) inside the splitter column. In this situation the MAPD decomposes exothermally inside the splitter column thus creating a hazardous situation due to excessive pressure and temperature.

Figure 3B:
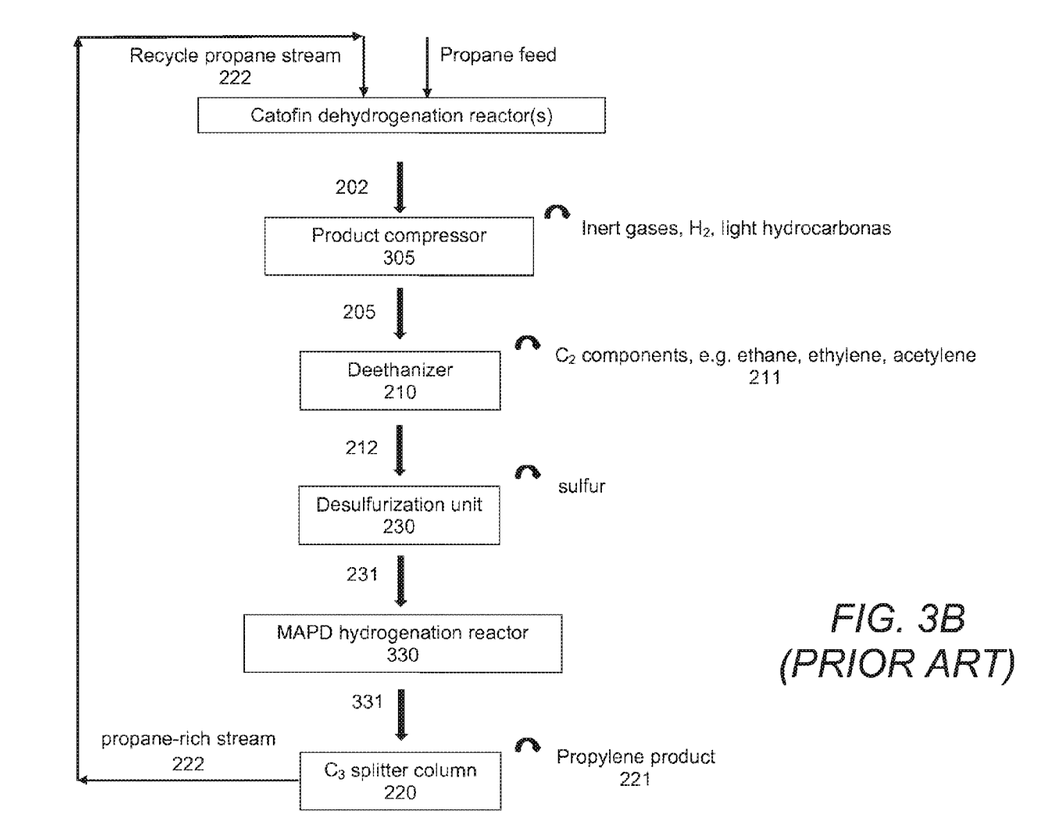
FIG. 3B is a flowchart providing a high-level overview of the major components of a conventional $C_3$ Catofin process, including the dehydrogenation reactors, product compressor, deethanizer, desulfurization unit, MAPD hydrogenation reactor, and $C_3$ splitter column.

Referring to the conventional Catofin process as shown FIG. 3A (process scheme) and FIG. 3B (flowchart), the propane not converted to propylene during the Catofin dehydrogenation process and the by-products are treated in a deethanizer 210 and a desulfurization unit 230 to form a MAPD-rich stream 231 prior to feed to the reactor 330, wherein the MAPD is hydrogenated. The reactor effluent 331, which is substantially free from MAPD, is fed to the splitter column 220, wherein the propylene product 221 is separated from a propane-rich stream 222. The propane-rich stream 222, which is also substantially free from MAPD and propylene, is further recycled by feeding it to front end of the $C_3$ Catofin process to be used as a recycled feed steam to the dehydrogenation process.

U.S. Pat. No. 8,013,201 describes an improved process for production of olefins wherein a high pressure product splitter is used to separate olefins produced in a dehydrogenation plant from residual paraffin feed stocks, but does not prevent the propylene product slip stream from being degraded and lost in MAPD removal.

U.S. Pat. No. 7,842,847 describes an improved process for separation of olefins from paraffins, such as propylene from propane, by using two product splitters in parallel, where one splitter operates at a lower pressure and the other operates at a higher pressure, but does not prevent the propylene product slip stream from being degraded and lost in MAPD removal.

U.S. Pat. No. 7,319,176 describes a process for selectively hydrogenating and removing acetylenic compounds from diene-rich hydrocarbon streams, but not the bottom stream from a $C_3$ deethanizer that is rich in propylene and propane and contains low levels of MAPD.

U.S. Pat. No. 6,218,589 describes a method for improving the operation of a propane-propylene splitter in a propane dehydrogenation process where the stream containing propylene, propane, hydrogen and trace quantities of MAPD is selectively hydrogenated to selectively saturate a majority of the trace quantities of MAPD. The resulting effluent from the selective hydrogenation zone is fractionated in a propane-propylene splitter to produce a high-purity propylene product stream, an unconverted propane stream which is introduced to the dehydrogenation zone and a small slip stream or side-cut containing MAPD which is introduced into the selective hydrogenation zone.

CN101993327B relates to a process of selectively hydrogenating and removing MAPD from refined propylene, but not the bottom stream from a $C_3$ deethanizer that is rich in propylene and propane and contains low levels of MAPD. The process described in CN101993327B also requires that the MAPD to be enriched into a stripping section and a tower kettle in the propylene rectification tower.

There is therefore a need for the reduction or elimination of the propylene production losses, generated by the established type of control for the concentration of the MAPD at the final product of the $C_3$ Catofin processes. It would be desirable to have a new process for the accurate control of the hydrogenation of the MAPD in $C_3$ Catofin processes, and certainly realize both economical and operational benefits that include an increase in product quality, elimination of production losses generated by the propylene slip stream, reduction of the amount of coke generated within the Catofin catalyst during the propylene production, increase in the stability of the catalyst bed installed in reactors of the $C_3$ Catofin processes, increase the safety at the operation of the splitter column and increment or extend the current life of the catalyst utilized at the reactors of $C_3$ Catofin.

BRIEF SUMMARY OF THE INVENTION

According to a first aspect the present disclosure relates to a process for purifying propylene, involving i) at least one of heating and pressurizing a first hydrocarbon stream comprising propylene, propane, methyl acetylene and propadiene, ii) contacting the first hydrocarbon stream with a first catalyst bed in the presence of hydrogen to at least partially hydrogenate the methyl acetylene and the propadiene to propylene and form a second hydrocarbon stream, iii) contacting the second hydrocarbon stream with a second catalyst bed to at least partially remove unreacted hydrogen from the second stream to form a third hydrocarbon stream, iv) contacting the third hydrocarbon stream with a third catalyst bed to remove residual hydrogen from the third hydrocarbon stream, wherein the first catalyst bed comprises a high-selectivity hydrogenation catalyst and the second catalyst bed and the third catalyst bed each comprises a low-selectivity hydrogenation catalyst.

In one embodiment, the first hydrocarbon stream is a bottom stream of a deethanizer. In one preferred embodiment, the first hydrocarbon stream is a bottom stream of a desulfurization unit which is located downstream of the deethanizer.

In one embodiment, the first hydrocarbon stream involves, i) at least 90% w/w of propylene and propane, and ii) no more than 0.1% w/w of a total amount of methyl acetylene and propadiene.

In one embodiment, the third hydrocarbon stream comprises 0.000001 w/w % or less of each of methyl acetylene, propadiene and hydrogen.

In one embodiment, the first hydrocarbon stream is a bottom stream of a deethanizer, and the method further comprises removing sulfur compounds from the first hydrocarbon stream.

In one embodiment, the method further comprises mixing the first hydrocarbon stream with a hydrogen stream.

In one embodiment, the first hydrocarbon stream is mixed with the hydrogen stream at a hydrogen/first hydrocarbon stream volume ratio of 1:1,000-10,000.

In one embodiment, the first hydrocarbon stream is heated to a temperature of higher than 34° C. and pressurized to a pressure of lower than 5,100 kPa.

In one embodiment, at least one of the contacting the second hydrocarbon stream with the second catalyst bed and the contacting the third hydrocarbon stream with the third catalyst bed further partially hydrogenates the methyl acetylene and the propadiene to propylene, propane, or both.

In one embodiment, at least one of the contacting the second hydrocarbon stream with the second catalyst bed and the contacting the third hydrocarbon stream with the third catalyst bed further at least partially hydrogenates the propylene produced from the propane dehydrogenation process and the propylene produced from hydrogenation of the methyl acetylene and the propadiene, to propane.

In one embodiment, the first catalyst bed and the second catalyst bed are located in a single reactor in a stacked-bed configuration, and the third catalyst bed is separated from the first catalyst bed and the second catalyst bed at the bottom of the same reactor or in a different reactor.

In one embodiment, the first catalyst bed, the second catalyst bed and the third catalyst are each located in individual, separate reactors.

In one embodiment, at least one of the first hydrocarbon stream, the second hydrocarbon stream, the third hydrocarbon stream and the hydrogen stream are in liquid phase.

In one embodiment, at least one of the contacting the first hydrocarbon stream, the contacting the second hydrocarbon stream and the contacting the third hydrocarbon stream are carried out at an average pressure of 2,500 kPa to 5,000 kPa and an average temperature 35° C. to 65° C.

In one embodiment, the method further comprises transporting the third hydrocarbon stream to a splitter column of the propane dehydrogenation process.

In one embodiment, the method further comprises adjusting the third hydrocarbon stream to operating conditions of the splitter column.

In one embodiment, the third catalyst bed comprises a single layer of the low selectivity hydrogenation catalyst.

In one embodiment, the first catalyst bed comprises 2 to 10 layers of the high selectivity hydrogenation catalyst.

In one embodiment, the second catalyst bed comprises 2 to 8 layers of the low selectivity hydrogenation catalyst.

In one embodiment, the high-selectivity hydrogenation catalyst comprises at least one selected from the group consisting of platinum, nickel and palladium and the low-selectivity hydrogenation catalyst comprises at least one selected from the group consisting of palladium, rhenium, cobalt, molybdenum, bismuth and tungsten.

In one embodiment, the third hydrocarbon stream is delivered to a splitter column, wherein concentration of methyl acetylene, propadiene (MAPD) and hydrogen is 0.000001 w/w % or less.

In one embodiment, the third hydrocarbon stream with reduced MAPD concentration provides a safer operation in the splitter column by preventing excessive temperature and pressure generated as a result of thermal oxidation of methyl acetylene and propadiene.

In one embodiment, a recycle stream with reduced MAPD concentration is delivered to a Catofin dehydrogenation process, wherein reduced MAPD concentration in the recycle stream prevent formation of coke in reactors of the Catofin dehydrogenation process, thus increasing catalyst life cycle.

In one embodiment, the third hydrocarbon stream is delivered to the splitter column, wherein concentration of methyl acetylene, propadiene (MAPD) and hydrogen is 0.000001 w/w % or preferably less than 0.0000001 w/w %. Accordingly, hydrogenating the methyl acetylene, propadiene (MAPD) may eliminate the use of a propylene slip stream; as it is conventionally used in $C_3$ Catofin processes to control the MAPD concentration. Additionally, hydrogenating the methyl acetylene, propadiene (MAPD) may further eliminate the loss of propylene as the propylene slip stream.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Referring now to the drawings, wherein like reference numerals designate identical or corresponding parts throughout the several views.

A non-limiting objective of the present disclosure to provide a process in which methyl acetylene and propadiene (MAPD) are selectively hydrogenated, without interfering with or changing with the nature or operating conditions or technology of the $C_3$ Catofin dehydrogenation process, and without affecting the propylene specificity the $C_3$ Catofin dehydrogenation process. In a particular embodiment the MAPD found in the feed stream to a splitter column of a $C_3$ Catofin dehydrogenation unit is hydrogenated to reduce fouling and coking during propane dehydrogenation, and to improve safety of the dehydrogenation by eliminating the risk of thermal oxidation of the MAPD in the splitter column. In this embodiment, up to 1 MT/h propylene is recovered.

Referring to FIGS. 3A and 3B showing a process scheme and a flowchart of a conventional $C_3$ Catofin process, respectively, the $C_3$ Catofin process is a non-oxidative dehydrogenation process where the dehydrogenation of the propane feed and the regeneration of the dehydrogenation catalyst, alternate in a cyclic or repetitive manner. Both dehydrogenation and regeneration are designed to run adiabatically (i.e. no net gain or loss of heat), with the dehydrogenation catalyst contacting the propane for very short cycles (e.g. 5-20 min, 7-15 min, 8-12 min, 8-10 min). There are typically multiple dehydrogenation reactors operating in parallel to allow catalyst regeneration to occur in some reactors (i.e. reactors on purge) while others are in operation (i.e. reactors on steam). During catalyst regeneration, or decoking, the reactor or the catalyst bed is purged with hot air to reheat the dehydrogenation catalyst and remove coke deposited on the catalyst bed during the endothermic dehydrogenation.

Besides the series of parallel dehydrogenation reactors, a conventional $C_3$ Catofin process also includes a product compressor 305 which cools and compresses the effluent stream 202 from dehydrogenation reactors and removes inert gases, hydrogen and light hydrocarbons from the effluent stream to produce a propylene-rich stream 205. The propylene-rich stream 205 undergoes purification through a deethanizer distillation column that remove $C_2$ components such as acetylene, ethylene and ethane to produce a stream 212 that is rich in propylene, propane, contains trace levels of methyl acetylene and propadiene but is substantially free of $C_2$ components including acetylene, ethylene, ethane, and hydrogen. The stream 212, which comprises propylene, propane, and MAPD, is then fed to a desulfurization unit for sulfur removal. The desulfurized stream 231 is then delivered to the reactor 330, wherein the MAPD is converted to propylene and a resulting MAPD-free stream 331 is further purified with a $C_3$ splitter column where the propylene product 221 is separated from a propane-rich stream 222.

Accordingly, a "deethanizer" as used herein refers to a distillation column that is located downstream of the series of dehydrogenation reactors and the product compressor of a $C_3$ Catofin process and upstream of a desulfurization unit, and is usually the first distillation column in the purification section of the $C_3$ Catofin process. A deethanizer removes $C_2$ components including ethane, ethylene, hydrogen and acetylene from a stream that is rich in propylene (propane dehydrogenation product) and propane (unconverted during dehydrogenation), that usually contains other dehydrogenation by-products such as but not limited to acetylene, ethylene, methyl acetylene (MA) and propadiene (PD).

Additionally, a desulfurization unit as used herein refers to a sulfur removal beds or an absorbers to remove elemental sulfur from sulfur containing compounds. Desulfurization unit is located downstream of the deethanizer and upstream of a MAPD hydrogenation reactor.

A "$C_3$ splitter column", or "$C_3$ propane-propylene splitter column" or "splitter column" as used herein refers to a distillation column that is located downstream of a MAPD hydrogenation reactor, and is usually the second distillation column in the purification section of the $C_3$ Catofin process. In some embodiments, multiple $C_3$ splitter columns may be installed downstream of the deethanizer in a $C_3$ Catofin process. A $C_3$ splitter column removes propane and other dehydrogenation by-products, including MAPD, from the propylene product. In accordance with the present disclosure, a reactor system having two separate reaction zones and two types of catalysts are utilized to hydrogenate the MAPD, contained in a bottom outlet stream of the deethanizer and/or desulfurization, at $C_3$ Catofin processes. The process permits the conversion of MAPD to propylene, by high and/or low selective hydrogenation, and in addition the recovery of a propylene slip stream, e.g., more than 1 MT/h, normally sent from the bottom of the splitter column to the dehydrogenation reactors.

The hydrogenation of MAPD to propylene is a well-known and established chemical reaction. The advantages of the process of the present disclosure therefore lie in features such as, but not necessarily limited to: (i). The MAPD found in the bottom stream from the deethanizer (i.e. stream 212 of FIGS. 2, 3A and 3B) of $C_3$ Catofin dehydrogenation processes is hydrogenated and therefore allows propylene to be recovered from the stream and additional propylene to be produced in the Catofin unit; (ii). The bottom stream exiting the deethanizer and/or desulfurization containing MAPD, propane and propylene (i.e. stream 212 of FIGS. 2, 3A and 3B), instead of entering the splitter column passes through one or more reactors in the hydrogenation reactor system with no internal recirculation; recycling or reprocessing of MAPD or hydrogen or reprocessing at the $C_3$ Catofin dehydrogenation unit; (iii). The process scheme is designed to increase the pressure of the inlet stream, achieve the required conditions to get the hydrogenation reactions of MAPD, a reactor designed to hydrogenate MAPD utilizing hydrogenation catalyst from any manufacturer, and where the catalyst complies with the requirements of the process, and it is guaranteed that the operation or product specificity of the $C_3$ Catofin process will not be altered in any manner; (iv). A system is designed to decrease and maintain the pressure of the outlet stream of the hydrogenation package at the normal value required by the $C_3$ Catofin processes; (v). The hydrogenation reactor system provided herein can eliminate the use of a propylene slip stream from the splitter columns, as used in conventional $C_3$ Catofin processes, and further eliminate the loss of propylene as a propylene slip stream; (vi). The hydrogenation reactor system and MAPD hydrogenation process described herein converts 100% of the trace amounts of MAPD found in the bottom outlet stream of the deethanizer and/or desulfurization, and does not require MAPD to be enriched prior to hydrogenation.

In carrying out the objectives of the present disclosure, the process for hydrogenating MAPD involves the utilization of equipment or a process scheme that adapts the operating conditions of the stream, normally fed to the splitter columns at $C_3$ Catofin processes, from low pressure and temperature, to higher pressure and temperature. The MAPD hydrogenation reaction takes place in presence/injection of hydrogen in a reactor, designed and equipped with two layers of catalysts: one high-selectivity hydrogenation and one low-selectivity hydrogenation catalyst with varying levels of MAPD hydrogenation efficiencies two different reaction zones, and a third layer containing the low-selectivity hydrogenation catalyst as the guard bed.

Figure 4:
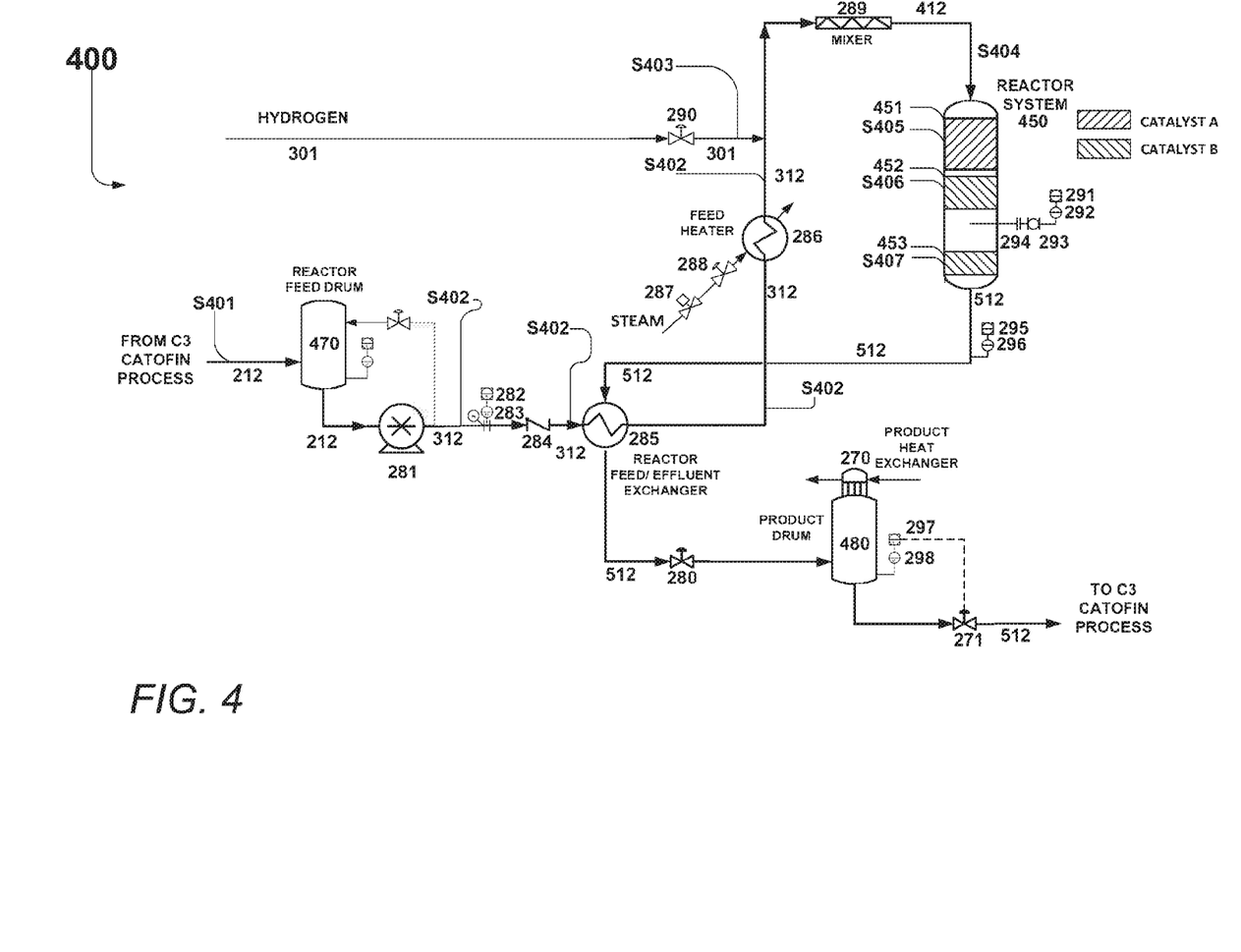
FIG. 4 illustrates a scheme for a process of hydrogenating methyl acetylene and propadiene (MAPD) from an effluent of a desulfurization unit in a $C_3$ Catofin process.

FIG. 4 illustrates a scheme for a process 400 for hydrogenating the methyl acetylene and propadiene (MAPD) from the feed stream from the deethanizer of a $C_3$ Catofin process to propylene according to one embodiment. In the preferable embodiment shown in FIG. 4, all components of the MAPD hydrogenation process 400, including hydrogenation reactor system 450 are added to become an auxiliary unit to a standard $C_3$ Catofin dehydrogenation unit. The process 400 begins when, at step S401, the deethanizer bottom stream 212 (or preferably the desulfurized stream after treatment in the desulfurization unit, i.e. stream 231) is taken out of the $C_3$ Catofin process. The deethanizer bottom stream 212 (or preferably the desulfurized stream after treatment in the desulfurization unit, i.e. stream 231) is rich in propylene and propane, both of constituting at least 90% w/w of the feed, preferably 90.0-99.9% w/w, more preferably 95.0-99.9% w/w. The MAPD contained in stream is an impurity or a by-product of Catofin propane dehydrogenation, in parts-per-million (ppm) levels, or less than 0.1% w/w, preferably 0.001-0.1% w/w, more preferably 0.01-0.1% w/w.

In a preferred embodiment, sulfur compounds are removed from the bottom stream 212 of the deethanizer 210 prior to feeding to the hydrogenation reactor system 450. These compounds may be removed in a desulfurization unit or a system that is installed as part of a standard $C_3$ Catofin dehydrogenation unit. Treating the stream 212 in the desulfurization unit prior to feeding to the hydrogenation reactor 450 may eliminate the need for regenerating the catalysts in the reactor 450. In another embodiment, in the absence of the desulfurization unit the bottom stream 212 of the deethanizer 210 is fed to the hydrogenation reactor system 450 without being treated in a desulfurization unit.

At step S402, the deethanizer bottom stream 212 (or preferably the desulfurized stream after treatment in the desulfurization unit, i.e. stream 231) is adapted in pressure and temperature to the required operating conditions of the hydrogenation reactor to hydrogenate the MAPD. In the embodiment shown in FIG. 4, the adaptation of temperature and pressure of the deethanizer bottom stream 212 (or preferably the desulfurized stream after treatment in the desulfurization unit, i.e. stream 231) is achieved in pressure by passing the stream through a centrifugal pump 281 connected to a check valve 284, and the temperature of the stream S402 is raised to an initial temperature using a cross heat exchanger 285, while the temperature is raised to a final temperature with another heat exchanger 286, wherein low pressure steam is used as the heating source. The steam flow is adjusted with a globe valve 288 to control the temperature. A solenoid valve 287 is also used to isolate the steam supply in case of a shutdown. The stream S402 is send at high pressure and temperature to a static mixer 289 where hydrogen is injected and mixed with S402. It should be noted that the MAPD hydrogenation process 400 of the present disclosure is not limited by other means of adjusting the temperature and pressure of the deethanizer bottom stream 212 (or the desulfurized stream after treatment in desulfurization unit), the amount and types of valves, pumps, separators, indicators, transmitters, elements, controllers, heat exchangers, condensers, compressors, coolers, actuators, modifiers and the like used throughout the step S402 and also the entire process 400.

Once the desired operating conditions are reached, the conditioned feed stream 31 which is in liquid phase, is mixed with a hydrogen stream 301, which is in gas phase, at step S403 to form a hydrogen-containing feed stream 412, and the hydrogen-containing feed stream 412 is further fed to the hydrogenation reactor system 450 at step S404. In the embodiment of FIG. 4, the hydrogen is mixed with the conditioned feed stream 312 via a static/mechanical mixer 289. Flow rate of the hydrogen stream 301 is controlled by a control valve 290. It is not necessary to subject the hydrogen stream 301 to a rectification tower to adjust the pressure and temperature of the hydrogen stream 301 prior to mixing with the conditioned feed stream 312, since the hydrogen is supplied from an upstream reciprocating compressor with a pressure of 3,000 kPa, more preferably 2,950 kPa and a temperature of 30° C., more preferably 26° C. Infused hydrogen in the hydrogen-containing feed stream 412 is in a liquid phase and has a temperature of lower than 65° C., preferably 40-60° C., more preferably 35-40° C., and a pressure of lower than 4500 kPa, preferably 2,500-4,500 kPa, more preferably 2,900-3,100 kPa, even more preferably 2,900-3,000 kPa, most preferably about 2,950 kPa, and the minimum or maximum flow of the stream 412 depends and varies according with the capacity of production of the $C_3$ Catofin process.

At step S405, the hydrogen-containing feed stream 412 is hydrogenated with the solubilized hydrogen with the high-selectivity catalyst (catalyst A) at the catalyst bed of the first reaction zone 451 of the reactor system 450. At least 85% of the MAPD, based on the total MAPD contained in the deethanizer bottom stream 212, is converted to propylene at the required operating conditions of the catalyst and in the presence of hydrogen, preferably 85.0-99.99% w/w, more preferably 90.0-99.99% w/w, most preferably 98.0-99.99% w/w.

Next, at step S406, hydrogen-containing feed stream 412 is further hydrogenated, without additional presence or injection of hydrogen, with the low-selectivity hydrogenation catalyst (catalyst B) at the catalyst bed of the second reaction zone 452 of the reactor system 450. The hydrogen in excess from the first reaction zone 451 is consumed at the second reaction zone 452. Thus, the low-selectivity hydrogenation catalyst at the catalyst bed of the second reaction zone 452 hydrogenates a further 0.01-15.0% w/w of the MAPD, based on the total MAPD contained in the original deethanizer bottom stream 212 from, $C_3$ Catofin dehydrogenation process, preferably 0.01-10.0% w/w, more preferably 0.01-2.0% w/w.

In order to minimize the propylene produced at the first reaction zone 451 from being hydrogenated to propane at the second reaction zone 452, the hydrogen-infused, solubilized at the hydrogen-containing feed stream 412 leaving the first reaction zone 451 and entering the second reaction zone 452 (not indicated in FIG. 4 but in FIG. 6 as 613) has a hydrogen/hydrocarbon volume ratio of 1:10,000-100,000, preferably 1:15,000-75,000, more preferably 1:25,000-50,000. To achieve this ratio at the second reaction zone 451, hydrogen is preferably mixed with the conditioned feed stream 312 at step S402 such that the hydrogen-containing feed stream 412 entering the first reaction zone 451 has a hydrogen/hydrocarbon volume ratio of 1:1,000-10,000, preferably 1:1,500-7,500, more preferably 1:2,500-5,000.

The liquid-phase outlet stream leaving the second reaction zone 452, which consists essentially of propane and propylene and is substantially free of MAPD (i.e. 99.0% w/w of the feed, preferably 99.0-99.99% w/w, more preferably 99.5-99.99% w/w (indicated in FIGS. 6 and 7 as 614), passes through a catalyst guard bed 453 at step S407. This liquid-phase outlet stream leaving the second reaction zone is also substantially free of hydrogen, inert gases such as nitrogen and $C_2$ components. The catalyst of the guard bed contains the same type of low-selectivity hydrogenation catalyst used at the second reaction zone 451 (i, e. Catalyst B). The function of the guard bed 453 is to eliminate any unreacted residual hydrogen from the previous first and second reaction zones of the reactor system. The prevalence of unreacted residual hydrogen in the outlet stream leaving the second reaction zone 452 is expected to at the end of run (EOR), when the catalysts installed at the first and second reaction zones have been considerably spent and may need replacement or regeneration. In such a scenario where residual hydrogen is found in the outlet stream, MAPD and propylene are hydrogenated until all hydrogen is consumed. The amount of MAPD that is hydrogenated in the guard bed, if any, preferably does not exceed 0.01% w/w, based on the total MAPD contained in the original deethanizer bottom stream 212, preferably 0.001-0.01% w/w, more preferably 0.001-0.005% w/w.

Accordingly, the high-selectivity hydrogenation catalyst serves to convert the MAPD to propylene in the first reaction zone, and the main purpose of the low-selectivity hydrogenation catalyst is to consume any hydrogen in excess in the second reaction zone and the guard bed. The high-selectivity hydrogenation catalyst has a MAPD selectivity of at least 85.0% w/w based a total amount of MAPD present in a sample or stream, preferably 85.0-99.9% w/w, more preferably 90.0-99.9% w/w, most preferably 95.0-99.9%. The low-selectivity hydrogenation catalyst has a MAPD selectivity of no higher than 75.0% w/w based on a total amount of MAPD present in a sample or a stream, preferably 25.0-75.0% w/w, more preferably 50.0-75.0% w/w. The low-selectivity hydrogenation catalyst also has the capability to hydrogenate MAPD in the presence of hydrogen, but instead of propylene, the product would be propane. Both the high- and low-selectivity hydrogenation catalysts are heterogeneous and fixed-bed catalysts. In some embodiments, a high-selectivity hydrogenation catalyst comprises at least one of platinum and palladium as primary catalytic metals, preferably palladium. In some embodiments, a low-selectivity hydrogenation catalyst comprises at least selected from palladium, rhenium, cobalt, molybdenum, bismuth and tungsten as primary catalytic metals, preferably cobalt. In certain embodiments, the high- and/or low-selectivity hydrogenation catalyst is mounted on an inert catalyst carrier, such as but not limited to silica, alumina and silica-alumina. In one embodiment, the high-selectivity hydrogenation catalyst and the low-selectivity hydrogenation catalyst contain palladium, wherein the amount of palladium in the high-selectivity hydrogenation catalyst is substantially higher than the amount of the low-selectivity hydrogenation catalyst. Furthermore, surface area of the high-selectivity hydrogenation catalyst may be in the range of 70-120 $m^2/g$, or preferably 80-110 $m^2/g$, or preferably 90-100 $m^2/g$, or preferably about 95 $m^2/g$, whereas surface area of the low-selectivity hydrogenation catalyst may be in the range of 50-90 $m^2/g$, or preferably 60-80 $m^2/g$, or preferably about 70 $m^2/g$. In another embodiment, the high-selectivity hydrogenation catalyst and the low-selectivity hydrogenation catalyst contain a transition metal selected from the groups 6-10 of the periodic table, preferably Pt, Pd, Ir and Re.

In some embodiments, an analysis indicator 291, an analysis transmitter 292, a flanged analysis element 293 and a flange 294 are installed between the second reaction zone 452 and the guard bed 453 to serve as a sample point, so that the composition, specifically the propane and propylene content of the outlet stream leaving the second reaction zone 452 can be analyzed, for example, chromatographically. Additional analyzers/sample points may be installed throughout the process 400. These analyzers are advantageously online analyzers.

The liquid-phase hydrogenation product stream 512 leaves the hydrogenation reactor system 450 and is returned to the Catofin dehydrogenation process as a feed stream to the splitter column from a product drum 480. The hydrogenation product stream 512 has a methyl acetylene or propyne content of equal or lower than 0.000001 w/w %, preferably 0.0000001-0.000001 w/w %, more preferably 0.0000005-0.000001 w/w %; a propadiene content of equal or lower than 0.000001 w/w %, preferably 0.0000001-0.000001 w/w %, more preferably 0.0000005-0.000001 w/w %; and a hydrogen content of 0.000001 w/w %, preferably 0.0000001-0.000001 w/w %, more preferably 0.0000005-0.000001 w/w %.

The temperature and pressure of the hydrogenation product stream 512 is conditioned to comply with the operating conditions of the inlet of the splitter column, as required by the $C_3$ Catofin process and the Catofin technology. In the embodiment of FIG. 4, after leaving the hydrogenation reactor system 450, the liquid-phase hydrogenation product stream 512 passes a temperature indicator 295, a temperature transmitter 296, and further a cross heat exchanger 285, wherein temperature of the stream 512 is reduced by the present cold stream 312. Additionally, a pressure control valve 280 is incorporated to adjust the pressure required by the $C_3$ Catofin process. Besides, a product heat exchanger 270 is also utilized to condense a vapor phase produced during the reduction of the pressure and adjust the temperature to the operating conditions as required by the splitter column in the $C_3$ Catofin process. The product heat exchanger 270 is fluidly connected to a product drum with a level transmitter 298, a level indicator 297, and a level control valve 271. The stream 512 with adjusted temperature and pressure is further delivered to the splitter column in the $C_3$ Catofin process.

The hydrogenation reactor system of the present disclosure includes at least three distinct reaction or hydrogenation zones (e.g., first reaction zone, second reaction zone and guardbed) that may be contained in a single reactor or a series of reactors. The reactors and/or number of reactors to be used in the hydrogenation reactor system will correspond with the hydraulic load of the Catofin dehydrogenation unit, the quantity of the required hydrogenation catalyst and needed space velocity for the hydrogenation of the MAPD. The hydrogen-containing feed stream 412 enters the hydrogenation reactor system and passes through from one reaction zone to another only once to reach a 100% MAPD conversion without being recirculated to any of the reaction zones and hydrogenation reactor(s) in the hydrogenation reactor system, while maintaining the liquid phase throughout the system. The reactor or reactors are preferably vertically oriented, so that the stream flows downwardly. Each reactor a preferably fixed bed reactor with one or more fixed catalyst beds, each packed with either the high-selectivity hydrogenation catalyst or the low-selectivity hydrogenation catalyst and/or a combination thereof, preferably each reactor section consists of only one type of catalyst. The catalyst bed of the first reaction zone is packed with 2-10 layers of the high-selectivity hydrogenation catalyst, preferably 3-8, more preferably 4-5. The catalyst bed of the second reaction zone is packed with 2-8 layers of the high-selectivity hydrogenation catalyst, preferably 3-7, more preferably 3-5. The guardbed is preferably packed with a single layer of the low-selectivity hydrogenation catalyst. In another embodiment, the guardbed is packed with a plurality of layers of the low-selectivity hydrogenation catalyst.

FIGS. 5-8 outline the various embodiments of the hydrogenation reactor system in accordance with the present disclosure.

Figure 5:
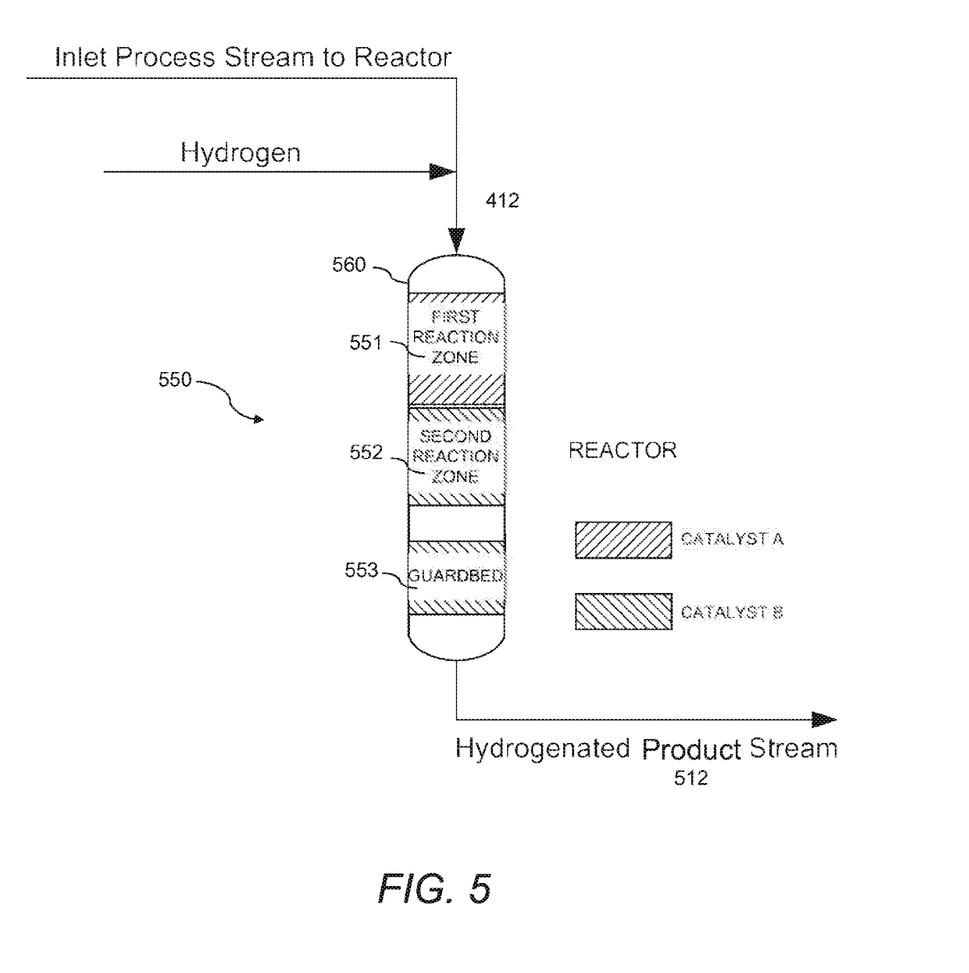
FIG. 5 illustrates a reactor system and a process for hydrogenating methyl acetylene and propadiene (MAPD) to propylene according to one embodiment, where the first and second hydrogenation catalysts are packed in a stacked-bed manner.

In one embodiment, as shown in FIG. 5, the hydrogenation reactor system 550 is a single-reactor system where the first reaction zone 551, second reaction zone 552 and the guard bed 553 are located in a single reactor 560, where the high-selectivity hydrogenation catalyst and the low-selectivity hydrogenation catalyst are packed in stacked-bed manner, where the high-selectivity hydrogenation catalyst and the low-selectivity hydrogenation are arranged in structured packing sections. Structured packings typically include thin corrugated metal plates or gauzes arranged in a way that they force fluids to take complicated paths through the catalyst bed, thereby creating a large surface area for contact between different phases. The guard bed 553 is a single layer of the low-selectivity catalyst, located at the bottom of the reactor, separated from the first and second reaction zones 551, 552.

Figure 6:
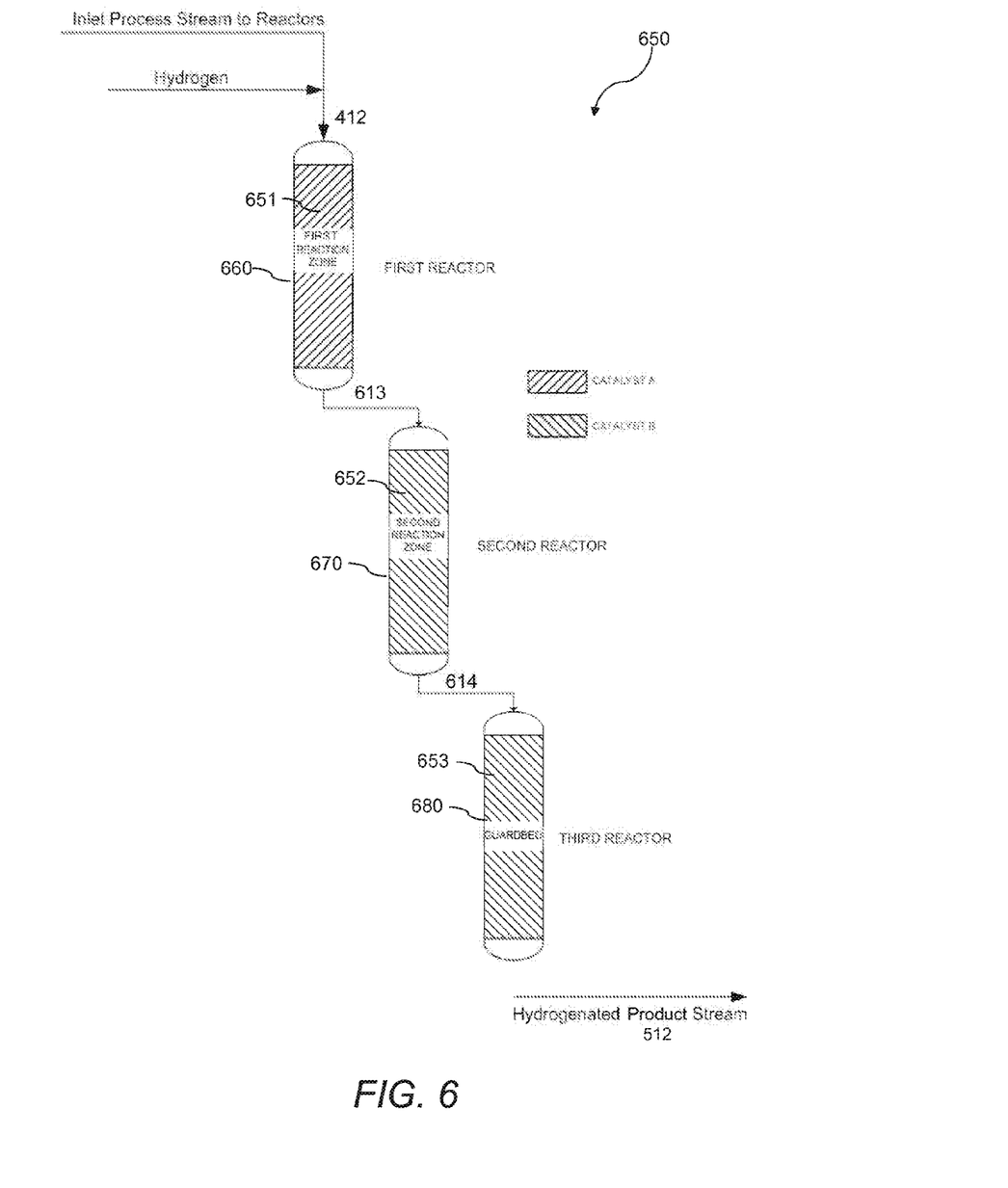
FIG. 6 illustrates a reactor system and a process for hydrogenating methyl acetylene and propadiene MAPD) to propylene according to one embodiment, where the first reaction zone, second reaction zone and guard bed are located in a series of separate reactors.

In an alternative embodiment, as shown in FIG. 6, the hydrogenation reactor system 650 includes a series of three reactors. The first reaction zone containing the high-selectivity hydrogenation catalyst 651, the second reaction zone containing the low-selectivity hydrogenation catalyst 652 and the guard bed containing the low-selectivity catalyst 653 are located separately in reactor 660, reactor 670 and reactor 680, respectively, with the reactors connected in series.

Figure 7:
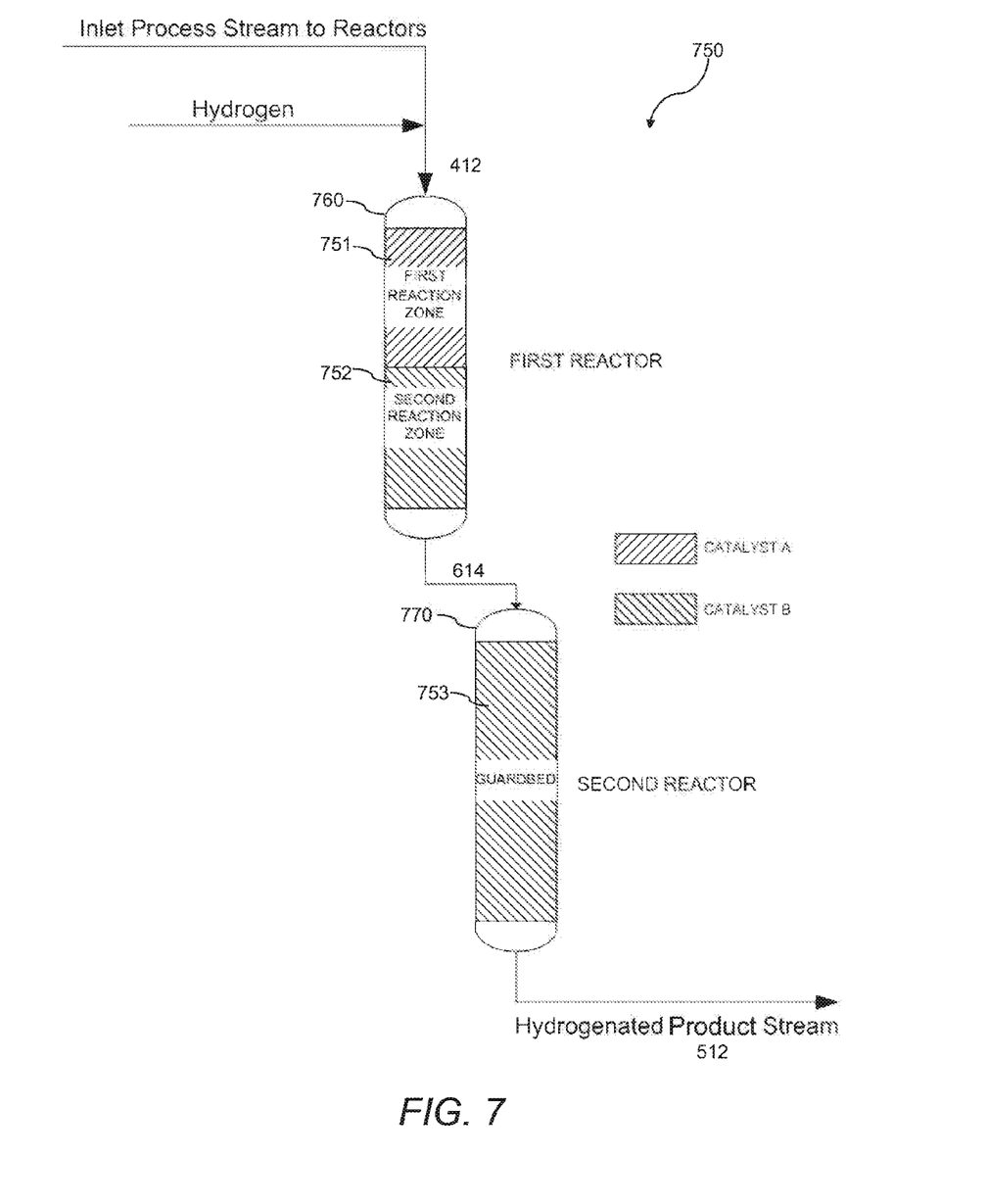
FIG. 7 illustrates a reactor system and a process for hydrogenating methyl acetylene and propadiene (MAPD) to propylene according to one embodiment, where the first and second reactions are located in one reactor while the guard bed is located in a separate reactor.

In another alternative embodiment, as shown in FIG. 7, the hydrogenation reactor system 750 includes two reactors. The first reaction zone containing the high-selectivity hydrogenation catalyst 751 and the second reaction zone containing the low-selectivity hydrogenation catalyst 752 are located in reactor 760 while the guard bed containing the low-selectivity catalyst 753 is located reactor 770.

Figure 8:
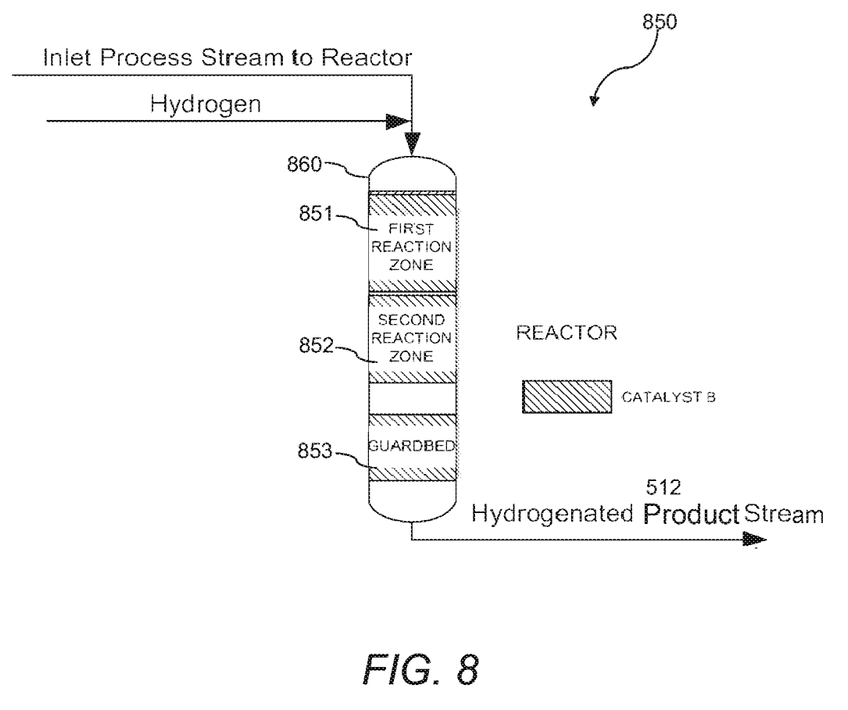
FIG. 8 illustrates a reactor system and a process for hydrogenating methyl acetylene and propadiene (MAPD) to propane according to one embodiment, where the first and second reaction zones are packed with only the second hydrogenation catalyst.

In yet another alternative embodiment, the hydrogenation reactor system includes a single or multiple (i.e. two or three) reactors but only one type of hydrogenation catalyst (high/low-selectivity). In FIG. 8, the hydrogenation reactor system 750 is as shown as having a single reactor 860 with the first reaction zone containing the low-selectivity hydrogenation catalyst 851, the second reaction zone containing the low-selectivity hydrogenation catalyst 852 and the guard bed containing the low-selectivity hydrogenation catalyst 853 packed in a stacked-bed manner. In this case, instead of propylene, the MAPD is converted to propane.

The operating conditions of the hydrogenation reactor system of the present disclosure include the following: an average pressure of 2,500-5,000 kPa, preferably 2,600-4,000 kPa, more preferably 2,900-3,200 kPa, even more preferably 2,950-3,100 kPa and an average temperature of 35-65° C., preferably 40-60° C., more preferably 45-60° C., even more preferably 50-60° C. If a plurality of hydrogenation reactors are used each may operate under distinct conditions from the others. Additional operating conditions include an average stream flow rate (i.e. average of stream 412 entering the first reaction zone, from the first reaction zone to the second reaction zone, and from the second reaction zone to the guard bed) of 155 MT/h-200 MT/h, preferably 160-190 MT/h, more preferably 173-183 MT/h. Such flow rates and pressure and temperature levels are varied within the defined ranges in accordance and depending on the stages of the life of the hydrogenation catalysts that are known as Start of Run (SOR), Middle of Run (MOR), and End of Run (EOR).

As used herein, a "Start of Run" or "SOR" refers to a stage of the life, a condition, or the performance of a hydrogenation catalyst (high-selectivity or low-selectivity) where the hydrogenation catalyst exhibits a catalyst fouling of 75.0% w/w or lower, preferably 60.0-75.0% w/w, more preferably 70.0-75.0%. The sources of catalyst fouling include the process itself (i.e. sulfur, coking deposits) and flue gas (i.e. flue ash deposits), and the catalyst fouling is calculated as the percentage of a spent hydrogenation catalyst weight based on the weight of an unused or new hydrogenation catalyst.

Similarly, a "Middle of Run" or "MOR", as used herein, refers to the stage of the life, the condition, or the performance of the high-selectivity or low-selectivity hydrogenation catalyst where the hydrogenation catalyst exhibits a catalyst fouling of no higher than 90.0% w/w, preferably 75.0-90.0% w/w, more preferably 80.0-90.0%.

An "End of Run" or "EOR", as used herein, refers to the stage of the life, the condition, or the performance of the high-selectivity or low-selectivity hydrogenation catalyst where the hydrogenation catalyst exhibits a catalyst fouling of 99.0% w/w, preferably 99.0-99.9% w/w, more preferably 99.5-99.9%. A hydrogenation catalyst reaching its EOR is indicative that the catalyst should either be replaced or regenerated.

There are a number of interrelated factors to be considered so that the operating parameters of the MAPD hydrogenation reactor system of the present disclosure can be more accurately determined and adjusted accordingly as a part of or ahead of a $C_3$ Catofin process. Such factors include but are not necessarily limited to the selection of the high- and low-selectivity hydrogenation catalysts, required operating conditions of the selected hydrogenation catalysts, the chemical composition of the $C_3$ Catofin feedstock (e.g. impurities), configuration of the reactor or reactors.

EXAMPLE

The following paragraphs describe a simulated MAPD hydrogenation process where all hydrogenation catalysts are at their Start of Run (SOR). It is to be understood that this simulated MAPD hydrogenation process is included herein as an example for strictly illustrative purpose, and is not intended to limit the scope of the invention.

A flow of 170 MT/h is fed from the desulfurization unit at a $C_3$ Catofin process, to the MAPD hydrogenation process scheme of FIG. 3. The main compounds of the stream include 0.037500% w/w of methyl acetylene or propyne, 0.017500% w/w of propadiene, 38.360000 w/w % of propylene, and 57.405000 w/w % of propane, and further detailed in Table 1.

Once the feed stream 412 enters the hydrogenation reactor system 450, the operating conditions of the stream are increased in pressure and temperature up to the ranges previously defined herein. The feed stream 412 is infused with hydrogen when a stream of pure hydrogen is fed and mixed with the stream 312 prior to entry of the feed stream 412 into the reactor system 450. Once the feed stream 412, in the presence of hydrogen is in contact with the high-selectivity catalyst at the first reaction zone 451, the MAPD is converted to propylene.

The outlet stream from the first reaction zone immediately enters the second reaction zone 452 and the hydrogen in excess, if any, is eliminated doing the partial conversion of the propylene contained on the outlet stream of the first reaction zone to propane. Due to the absence of hydrogen, the outlet stream from the second reaction zone 452 passes through the guard bed 453 without being reacted with. The outlet streams from the first and second reaction zones are not indicated in FIG. 4.

The outlet stream 512 exiting the hydrogenation reactor system 450 is then processed by having its temperature and pressure decreased up to the requirements of the inlet stream of the splitter column at the $C_3$ Catofin process, i.e. a temperature of 9-14° C. and a pressure of 900-1,250 kPa. The splitter column of the $C_3$ Catofin receives this outlet stream 512 as feed, without any trace MAPD and hydrogen (i.e. ≤0.000001% w/w, preferably 0.000001-0.00001% w/w, more preferably 0.000001-0.000005% w/w).

The compositions of streams at various stages of the simulated MAPD hydrogenation process are shown in Table 1.

| | Stream Number | | | |
|---|---|---|---|---|
| | 212 | 301 | 412 | 512 |
| | Stream Name | | | |
| Component Name | Feed from C$_3$ deethanizer Composition w/w % | Hydrogen Composition w/w % | Hydrogen + Feed from C$_3$ deethanizer Composition w/w % | Hydrogenation reactor system outlet Composition w/w % |
| 1-3-Butadiene | 0.040000 | 0.000000 | 0.039997 | 0.000000 |
| Benzene | 0.500000 | 0.000000 | 0.499962 | 0.499962 |
| 1-Butene | 0.080000 | 0.000000 | 0.079994 | 0.079994 |
| cis-2-Butene | 0.060000 | 0.000000 | 0.059995 | 0.059995 |
| Ethane | 0.080000 | 0.000000 | 0.079994 | 0.079994 |
| N-Pentane | 0.440000 | 0.000000 | 0.439967 | 0.439967 |
| I-Butane | 1.810000 | 0.000000 | 1.809863 | 1.809863 |
| Propyne | 0.037500 | 0.000000 | 0.037497 | 0.000000 |
| N-Butane | 0.080000 | 0.000000 | 0.079994 | 0.122972 |
| Propadiene | 0.017500 | 0.000000 | 0.017499 | 0.000000 |
| Propane | 57.405000 | 0.000000 | 57.400668 | 57.440360 |
| Propylene | 38.360000 | 0.000000 | 38.357105 | 38.376975 |
| Toluene | 0.130000 | 0.000000 | 0.129990 | 0.129990 |
| trans-2-Butene | 0.840000 | 0.000000 | 0.839937 | 0.839937 |
| p-Xylene | 0.120000 | 0.000000 | 0.119991 | 0.119991 |
| Hydrogen | 0.000000 | 100.000000 | 0.007563 | 0.000000 |

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for purifying propylene obtained from a propane dehydrogenation process by converting dehydrogenation by-products comprising:
receiving a hydrogen-free first hydrocarbon stream comprising methyl acetylene, propadiene, butadiene, propane and propylene from a propane dehydrogenation process;
at least one step of heating and pressurizing the first hydrocarbon stream;
contacting the first hydrocarbon stream with a first catalyst in the presence of injected hydrogen to at least partially hydrogenate methyl acetylene and propadiene and form a second hydrocarbon stream;
contacting the second hydrocarbon stream with a second catalyst to complete the hydrogenation of methyl acetylene and propadiene, and removing at least a portion of residual hydrogen to form a third hydrocarbon stream comprising propane and propylene in an amount of 99.0-99.99% w/w and less than 0.000001% w/w of methyl acetylene, propadiene, butadiene and hydrogen; and
contacting the third hydrocarbon stream with a third catalyst which catalyzes removal of residual hydrogen from the third hydrocarbon stream at a level of less than 0.000001% w/w to form a hydrogen-free third hydrocarbon stream;
wherein
the first catalyst has a selectivity towards hydrogenation of methyl acetylene and propadiene to propylene of at least 85% w/w and a surface area of 70-120 m$^2$/g; and
each of the second and the third catalysts has a selectivity towards hydrogenation of methyl acetylene and propadiene to propylene of no more than 75% w/w and a surface area of 50-90 m$^2$/g;
wherein the first catalyst is located in a first catalyst bed, the second catalyst is located in a second catalyst bed and downstream of the first catalyst bed, and the third catalyst is located in a third catalyst bed and downstream of the second catalyst bed, and
wherein the hydrogen-free third hydrocarbon stream comprises propane and propylene in an amount of 99.0-99.99% w/w and less than 0.000001% w/w hydrogen, methyl acetylene, propadiene, and butadiene.

2. The method of claim 1, wherein the first, second and third hydrocarbon stream are in the liquid phase.

3. The method of claim 1, wherein the first, second and third catalysts are in a single reactor.

4. The method of claim 1, wherein the first catalyst has a selectivity towards hydrogenation of methyl acetylene and propadiene to propylene of 90.0-99.9% w/w and a surface area of 90-100 m$^2$/g; and
each of the second and the third catalysts has a selectivity towards hydrogenation of methyl acetylene and propadiene to propane of 25-75% w/w and a surface area of 60-80 m$^2$/g.

5. The method claim 1, wherein an average pressure of the contacting of the first and second hydrocarbon stream is 2,500-5,000 kPa and with an average temperature of 35-65° C.

6. The method of claim 5, wherein an average pressure of an inlet stream to the unit containing the first and the unit containing the second catalyst is 900-1,250 kPa and with an average temperature of 9-14° C.

7. The method of claim 1, wherein the first hydrocarbon stream is mixed with the injected hydrogen at a hydrogen/first hydrocarbon stream volume ratio of 1:1,000-10,000.

8. The method of claim 4, wherein the first, second and third catalysts are palladium catalysts.

9. The method of claim 2, wherein the first, second and third catalysts are in a single reactor.

10. The method of claim 9, wherein the first catalyst has a selectivity towards hydrogenation of methyl acetylene and propadiene to propylene of 90.0-99.9% w/w and a surface area of 90-100 m$^2$/g; and each of the second and the third catalysts has a selectivity towards hydrogenation of methyl acetylene and propadiene to propane of 25-75% w/w and a surface area of 60-80 m$^2$/g.

11. The method of claim 10, wherein an average pressure of an inlet stream to the unit containing the first catalyst and the unit containing the second catalyst is 2,500-5,000 kPa and with an average temperature of 35-65° C.

12. The method of claim 11, wherein an average pressure of an inlet stream to the unit containing the first catalyst and the unit containing the second catalyst is 900-1,250 kPa and with an average temperature of 9-14° C.

13. The method of claim 12, wherein the first hydrocarbon stream is mixed with the injected hydrogen at a hydrogen/first hydrocarbon stream volume ratio of 1:1,000-10,000.

14. The method of claim 13, wherein the first, second and third catalysts are palladium catalysts.

* * * * *